United States Patent [19]

White et al.

[11] Patent Number: 4,874,359

[45] Date of Patent: Oct. 17, 1989

[54] POWER INFUSER

[76] Inventors: Frederick R. White, 3656 Glazier Way, Ann Arbor, Mich. 48105; Roy E. Bolles, 50 Woodland Dr., Iowa City, Iowa 52240

[21] Appl. No.: 132,967

[22] Filed: Dec. 14, 1987

[51] Int. Cl.[4] .............................................. A61M 37/00
[52] U.S. Cl. ................................. 604/4; 128/DIG. 12; 128/DIG. 13; 604/67; 604/113; 604/118; 604/122; 604/153
[58] Field of Search ........................................ 604/4–6, 604/51–53, 67, 113, 114, 118–123, 151–153, 185, 317–319, 405, 406; 128/DIG. 3, DIG. 12, DIG. 13, 399, 400

[56] References Cited

U.S. PATENT DOCUMENTS

| | | | |
|---|---|---|---|
| 3,191,600 | 6/1965 | Everett | 604/319 |
| 3,896,733 | 7/1975 | Rosenberg | 604/4 |
| 4,398,872 | 8/1983 | Fleenor et al. | 604/151 |
| 4,401,431 | 8/1983 | Arp | 604/4 |
| 4,466,804 | 8/1984 | Hino | 604/118 |
| 4,565,500 | 1/1986 | Jeensalute et al. | 604/67 |
| 4,623,333 | 11/1986 | Fried | 604/122 |
| 4,705,508 | 11/1987 | Karnavas et al. | 604/4 |
| 4,747,826 | 5/1988 | Sassano | 604/52 |
| 4,759,749 | 7/1988 | Verkaart | 604/113 |

OTHER PUBLICATIONS

Rapid Infusion Device May Untangle Trauma Care, Welcome Trends in Anesthesiology, Park Row Publishers, Inc. vol. 3, no. 4, (8–85).
Kang et al., "Intraoperative Changes in Blood Coagulation" Anesth. Analg., 64:888–896, (1985).
Estrin et al., A New approach to Massive Blood Transfusion During Pediatric Liver Resection, Surgery, 664–670, (6–86).
Jeretin, Dilemmas in Anesthesiology Actu Chir Iugol, 27, Supple 2, 13–18, (1980).
Sassano et al., Limitations of Conventional Transfusion Systems, ASA Abstract, Anesthesiolgy A152, vol. 63, no. 3A, (9–85).
Philip et al., Pressurized Infusion System for Fluid Resuscitation Anesth Analg. 63:779–781, (1984).
Sassano, The Rapid Infusion System, Ch. 10, Winto D. M. et al. Hepatic Transplonations, Praeger Publishers, New York N.Y. (1986).

Primary Examiner—C. Fred Rosenbaum
Assistant Examiner—Mario Costantino
Attorney, Agent, or Firm—James M. Deimen

[57] ABSTRACT

A modular, power augmented medical infusion apparatus to provide rapid transfusion of relatively large quantities of blood, blood components, colloid, and fluids to patients. All components of the infuser that contact blood are sterlie, disposable, and easily assembled. Disassembled or partially assembled the components are also easily transportable. The major components comprise a pair of filtered cardiotomy reservoirs, an air embolus sensor, a modular double roller pump, a heat exchanger, a bubble trap-filter and disposable fluid conduits. The bubble trap-filter is located in the distal most location of the recirculating loop just upstream of the Y-connector to the patient and the air sensor just downstream of the cardiotomy reservoir in the proximal location of the recirculating loop. The experimental infuser has been safely and successfully used with patients undergoing liver transplantation, combined liver and kidney transplantation, major vascular surgery, and other operations associated with large rapid transfusion requirements.

22 Claims, 2 Drawing Sheets

POWER INFUSER

BACKGROUND OF THE INVENTION

The field of the invention pertains to the transfusion of blood, blood components, colloids and other fluids to patients and, in particular, to procedures wherein large quantities of blood may be unavoidably lost from the patient through bleeding. Such losses occur, for example, during liver transplantation and major vascular surgery. Such losses may also occur in response to serious accident or wound.

Pertinent to rapid large quantity infusion are the following related references:
1. Rapid Infusion Device May Untangle Trauma Care, Wellcome Trends in Anesthesiology, Park Row Publishers, Inc., Vol. 3, No. 4, August 1985.
2. Kang, Yoo Goo, M.D., Martin, Douglas J., M.D., Marquez, Jose, M.D., Lewis, Jessica H., M.D., et al. Intraoperative Changes in Blood Coagulation and Thromboelastographic Monitoring in Liver Transplantation. Anesth Analg 64:888–96, 1985.
3. Estrin, J. A., Belani, K. G., Karnava, A. G., Petersen, R. J., Leonard, A. S., Buckley, J. J.: A New Approach to Massive Blood Transfusion During Pediatric Liver Resection. Surgery 664–70, June, 1986.
4. Jeretin, S.: Dilemmas in Anesthesiology. Acta. Chir. Iugol., 27 Suppl. 2, 13–8. 1980.
5. Winter, P. M., Kang, Y. G. Hepatic Transplantation, Praeger Publishers, New York, N.Y., 1986.

There also have recently been marketed a RAPID INFUSION SYSTEM from Haemonetics Corporation of 400 Wood Road, Braintree, MA 02184.

Unfortunately, the infusion apparatus available tends to be difficult to control and monitor when large scale rapid infusion is attempted. The apparatus is also difficult to transport and to clean and sterilize. To overcome the disadvantages of the current available infusion apparatus the applicant has developed and experimentally tested the infuser disclosed below.

SUMMARY OF THE INVENTION

The power infuser comprises a modular, power augmented mechanical infusion apparatus for the infusion or transfusion of pre-warmed, filtered blood, colloid and crystalloid to patients who required large quantities of these blood components to be rapidly transfused. The object is to assist in the orderly, safe, stable and efficient resuscitation of patients who are suffering from massive hemorrhage, extensive surgical bleeding, or who may require large immediate quantities of blood, fluid, colloid or crystalloid for other reasons.

The major components comprise a pair of filtered cardiotomy reservoirs, a modular double roller pump, an air embolus sensor, a heat exchanger, a bubble trap filter and disposable fluid conduits. The bubble trap-filter is located in the distal most location of the recirculating loop just upstream of the Y-connector to the patient and the air sensor just downstream of the cardiotomy reservoir in the most proximal portion of the recirculating loop.

All components of the infuser that contact blood are sterile, disposable, and easily assembled. Disassembled or partially assembled the components are easily transportable. With the modular design the infuser can be easily disassembled and stored in areas of limited space. With slight modification the infuser can be adapted for use in ambulances, airplanes or helicopters. The experimental infuser has been safely and successfully used by the applicant, an anesthesiologist, in patients undergoing liver transplantation, major vascular surgery, and other operations involving large transfusions. The infuser has been approved for general clinical use by the University of Michigan Medical School Institutional Review Board.

DESCRIPTION OF THE PREFERRED EMBODIMENT

Figure 1:
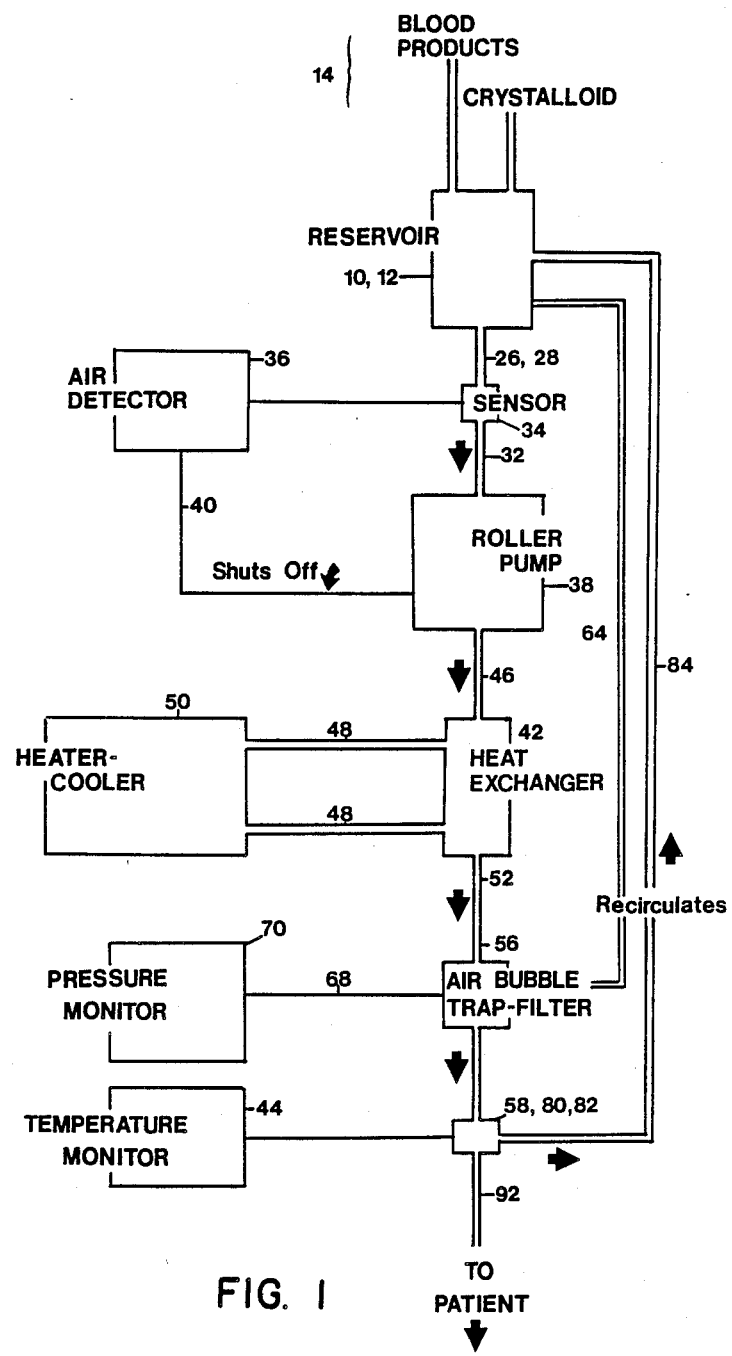
FIG. 1 is a simplified flow diagram of the power infuser.
Figure 2:
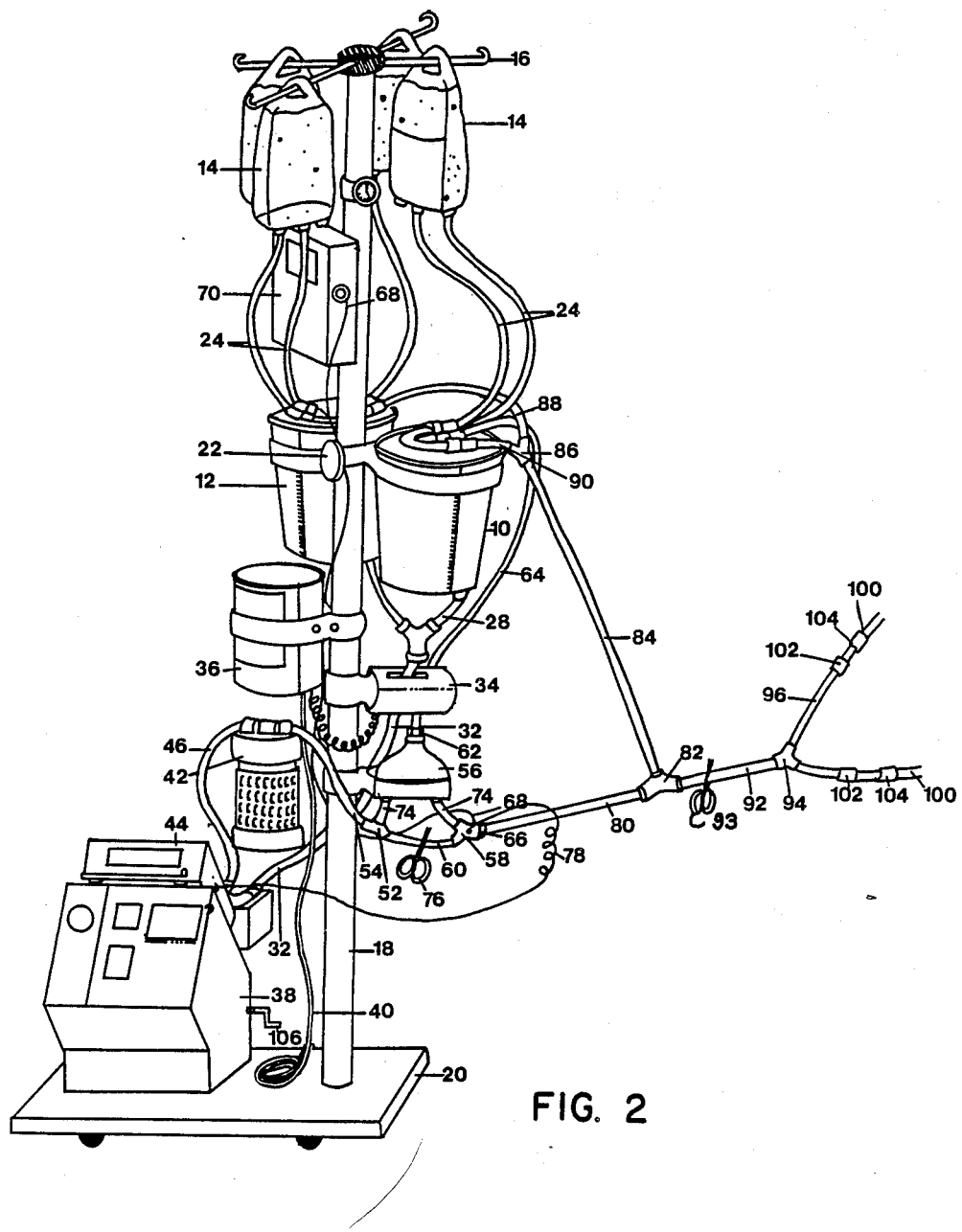
FIG. 2 is a perspective view of the power infuser.

As illustrated in FIGS. 1 and 2 the infuser comprises a pair of cardiotomy reservoirs 10 and 12 which are supplied from hanging multiple bags 14 such as intravenous fluid bags, blood bags, or other solution containers with the fluid to be administered. The bags 14 are hung from extension arms 16 on a pole 18 that in turn is detachably mounted on a base 20. The cardiotomy reservoirs 10 and 12 are removably and adjustably clamped at 22 to the pole 18.

Suitable as reservoirs 10 and 12 are two SC4000F, filtered cardiotomy reservoirs which can hold 6000 ml (3000 ml in each) of blood, blood components, colloid or fluid and are available from Sci Med Life Systems, Inc. of 13000 County Road 6, Minneapolis, Minn. 55441. The 6000 ml of blood is slightly more than the total blood volume of an average size adult patient (70 kg). Thus, the infuser has the potential of replacing the entire blood volume of a patient who has suddenly exsanguinated or is rapidly bleeding. The reservoirs 10 and 12 each have five ports through which additional blood or fluid can be rapidly loaded into the reservoirs of the infuser for the treatment of ongoing bleeding or other infusion requirements. The reservoirs have both a filter and defoaming sock to remove particulate debris in the blood and to remove small air bubbles that are entrained in the blood during use of the infuser.

In FIG. 2 the four bags 14 shown are connected by one-half inch diameter loading tubes 24 to two ports of each reservoir 10 and 12. Leading from the reservoirs 10 and 12 are two perfusion tubing conduits 26 and 28 which are joined together by a Y-connector 30 leading to one tube 32. The conduits or tubes 26, 28 and 32 are ⅜ inch diameter polyvinyl chloride (PVC) tubing. This tubing as well as other tubing disclosed below is available from Electromedics, Inc. of 7337 South Revere Parkway, Englewood, Colo. 80112.

The tube 32 extends through a SARNS air bubble detection system comprising a sensor 34 and detector 36 to a SARNS 7000 double-roller pump 38 attached to the SARNS modular base 20. All SARNS devices are available from Sarns, Inc., 6200 Jackson Road, Ann Arbor, Mich. 48103. The SARNS air bubble detection system 34 and 36 detect air bubbles by an infra-red analyzer and, upon such detection, signals through electrical conduit 40 the SARNS pump 38 to stop and give an audible alarm.

The SARNS pump 38 includes a digital display of the calculated rate of blood flow through the roller pump. The pump 38 provides the power necessary to circulate blood through the heat exchanger 42 and reservoir-filtering systems of the infuser and to provide an augmented means of variable rate transfusion. The pump 38 is capable of variably delivering blood to a patient at a rate of 100 to over 2500 ml/min. (cc's min.). Atop the pump 38 is a SHILEY DPSI temperature monitor 44 available from Shiley Cardiopulmonary Division 17600 Gillete Avenue, Irvine, Calif. 92714 for the purpose of continuously monitoring the blood temperature.

Leading from the pump 38 is a conduit 46 of ⅜ inch diameter PVC to the heat exchanger 42. An ELECTROMEDICS D1080 blood cardioplegia delivery system heat exchanger available from Electromedics, Inc. and manufactured by Dideco, S.P.A. 41037 Mirandola, Italy is a suitable heat exchanger to warm or cool the blood with the aim being to maintain a blood temperature in the infuser at a constant 37° C. The heat exchanger is supplied with water at a suitable temperature through tubes 48 connected to a heater-cooler 50.

Exiting the heat exchanger 42 the blood passes through ⅜ inch diameter conduit 52 to Y-connector 54. One limb of the Y-connector 54 leads through an arterial bubble trap-filter 56 to a Y-connector 58. The arterial bubble trap-filter is available from Olson Medical Sales, Inc., 28 Howe Street, Ashland, Mass. 01721. The other limb of the Y-connector 54 leads through a bypass tube 60 to Y-connector 58. Thus, blood can be by-passed through ½ inch diameter PVC bypass tube 60 to bypass the air bubble trap-filter 56. A filter with a nominal filtering capability of 33 microns is incorporated into the air bubble trap-filter 56.

Atop the filter 56 is a three way stopcock 62 which allows air trapped in the filter 56 to be evacuated. Attached to a second stopcock port is a tube 64 which extends to the cardiotomy reservoir 10. The tube 64 permits the air trapped in the filter 56 to be recycled to the reservoir 10 without opening the infuser loop to the environment. A transducer in the Y-connector 58 and conduit 68 lead to a pressure sensing monitor 70 to provide continuous monitoring of the pressure in the conduit just downstream of the Y-connector 58. A port in a second stopcock 66 permits blood samples for analysis to be drawn. The transducer and pressure sensing monitor are available from DLP, Inc., 620 Watson, S.W., Grand Rapids, Mich. 49504.

If the air bubble trap-filter 56 becomes clogged with debris during use of the infuser, by clamping the tubing 74 leading to and from the trap-filter 56 and opening the clamp 76 on the bypass tube 60, the trap-filter can be quickly changed without interrupting the recirculation of the infuser.

Also connected to the Y-connector 58 is a temperature monitoring probe and electrical connection 78 leading to SHILEY DPSI unit 44 which provides a continuous digital display of blood temperature.

From the Y-connector 58 and stopcock 66 a conduit 80 leads to the Y-connector 82 and a recirculating link or tube 84 back to the cardiotomy reservoirs 10 and 12 by way of the Y-connector 86 and tubes 88 and 90. With the pump 38 operating there is constant recirculation, filtering and warming of the blood or fluid in the loop when not being infused into the patient. The other limb or tube 92 is equipped with a clamp 93 and leads to a Y-connector 94 with two limbs or tubes 96 and 98 so that upon the release of clamp 93 the blood or fluid can be infused into the patient through two access ports or catheters.

Between the final infusion tubing 100 the tubing of each limb is interrupted by a double stopcock 102 and 104. One of each of these stopcocks may be attached to a standard intravenous infusion system for transfusion of blood or fluid in the standard fashion. The other stopcock is available for the attachment of a syringe for injection or aspiration of blood or fluid.

Attached to the final tubing 100 is a male luer lock connector (not shown) which may be connected to a variety of standard intravenous cannulae which are inserted in a vein at any one of a number of locations. Generally a large diameter, 8.0 or 8.5 Freah, ARROW catheter is used for this purpose. Such catheters are available from Arrow International, Inc., Hill and George Avenues, Reading, Penna. 19610. Internal jugular veins, antecubital veins, femoral veins, and subclavian veins have all been used safely and successfully as the final point of transfusion to the patient.

In the event of electrical failure the pump 38 includes a handle 106 to manually rotate the pump so that the infuser can continue to be operated. As best shown in FIG. 2 all of the elements of the infuser with the exception of the pump 38 and temperature probe unit 44 are removably clamped or hung on the pole 18 and the pole can be removed from the base 20 which in turn is affixed to the pump 38. Thus, all of the elements can be disassembled and assembled easily for transportation and storage. With the use of perfusion connectors for the Y-connectors and disposable tubing the infuser can be quickly assembled for use and when use is completed all of the tubing, connectors and stopcocks thrown out. The infuser can then be either disassembled or new disposable items reconnected for the next patient.

As optional items for the infuser the cardiotomy reservoirs 10 and 12 can each be equipped with a buoyant ball to occlude the outlet of the reservoir when it empties of infusate. The ball creates a ball value in the reservoir that is open only when sufficient fluid or blood is present in the reservoir.

Heparin bonded tubing may be used for the distal most portions of the tubing to prevent clotting that otherwise might occur if non-anticoagulated blood from the patient reflexes into the tubing through the connections to the patient.

The components noted above are currently the preferred devices for the infuser, however, a number of alternate components have been successfully tested in the infuser. For example, the cardiotomy reservoirs and tubing may be BENTLEY BCR 3500 from Baxter Health Care, Inc., 17221 Redhill, Santa Ana, Calif. 92711 and the bubble-trap filter a DELTA K-37 unit from Delta Medical Industries, 1579 Sunland Lane, Cost Mesa, Calif. 92626. Omnis Surgical, Deerfield, Ill. and more recently Pharmaceal, 27200 Tourney Road, Valencia, Calif. 91355 are suppliers of a suitable heat exchanger. Other suitable components may be substituted for these components without substantially departing from the spirit of this invention as defined by the claims below.

We claim:

1. A power infuser comprising at least one cardiotomy reservoir and means to charge the reservoir with fluid, fluid conduit means providing a recirculatory loop communicating from and returning to the reservoir, an air embolus sensor in a near downstream location relative to the reservoir in the loop, a non-fluid contact pump in the loop downstream of the air embolus sensor, means to control the temperature of the fluid in the loop, a bubble trap-filter in a far downstream location relative to the reservoir in the loop said bubble trap-filter having an inlet and outlet, said fluid conduit means including tubing means in fluid communication with the filter outlet at one end and with the reservoir at a second end to complete the recirculatory loop, and separate means in fluid communication with the tubing means between the bubble-trap filter outlet and reservoir to selectably discharge fluid from the loop to a patient, said discharge means being downstream of the bubble trap-filter.

2. The power infuser of claim 1 including a first conduit which bypasses the bubble trap-filter and a second bypass from the bubble trapfilter to the reservoir.

3. The power infuser of claim 2 wherein said second bypass permits aspiration of air in the bubble trap-filter directly to the reservoir.

4. The power infuser of claim 1 including fluid temperature and pressure sensing means located just downstream of the bubble trap-filter and monitoring means connected to the fluid temperature and pressure sensing means.

5. The power infuser of claim 1 including pressure sensing means located just downstream of the bubble trap-filter and a pressure monitor in communication with said pressure sensing means adapted to continuously measure and display the fluid pressure as fluid exits the bubble trap-filter.

6. The power infuser of claim 1 wherein said proximal air embolus sensor is in communication with the pump whereby said pump is disabled upon detection of an embolus.

7. The power infuser of claim 6 including means to selectably override the air embolus sensor and operate the pump despite air in the fluid passing through the sensor.

8. The power infuser of claim 1 wherein said bubble trap-filter nominal capability is 33 microns.

9. The power infuser of claim 1 including means to defoam and filter fluid in the cardiotomy reservoir whereby operation of the pump causes continuous recirculation of fluid in the loop with filtering in the reservoir and the bubble trap-filter.

10. The power infuser of claim 1 wherein the recirculatory loop and means to selectably discharge fluid from the loop to a patient are capable of providing fluid at a rate of up to 2500 cc/min.

11. The power infuser of claim 1 wherein the cardiotomy reservoir, air embolus sensor and bubble trap-filter are detachably mounted on a vertical support in full view of the operator of the infuser.

12. The power infuser of claim 1 wherein a base supports the pump and a vertical pole, said cardiotomy reservoir, heat exchanger, bubble trap-filter and air embolus detector being detachably mounted on the pole.

13. The power infuser of claim 1 wherein the fluid conduit of the recirculatory loop is transparent and clearly in view to the operator of the infuser.

14. The power infuser of claim 1 wherein the means to selectably discharge fluid from the recirculatory loop comprise a Y-connector in the loop and a fluid conduit in fluid communication with the Y-connector for communication with a patient, said fluid conduit to the patient including means to open and close the conduit and means to provide communication with a separate intravenous infusion system.

15. The power infusion of claim 14 including a second Y-connector in the fluid conduit to the patient providing branched conduits to the patient, the branched conduits each including means to provide communication with a separate intravenous infusion system and means for access with a syringe.

16. The power infuser of claim 1 wherein the cardiotomy reservoir is of sufficient capacity to transfuse the entire blood volume of an adult patient.

17. The power infuser of claim 1 wherein the cardiotomy reservoir includes automatic means to occlude the outlet of the reservoir just prior to exhaustion of fluid in the reservoir to thereby prevent air from passing through the outlet.

18. The power infuser of claim 1 including means to manually operate the pump.

19. The power infuser of claim 1 wherein all fluid conduits and elements in direct contact with the fluid are disposable.

20. The power infuser of claim 1 wherein the means to charge fluid to the cardiotomy reservoir comprise intravenous fluid bags located above the reservoir.

21. The power infuser of claim 20 wherein the recirculating fluid is whole blood anti-coagulated as supplied from the intravenous fluid bags.

22. A power infuser comprising at lesat one cardiotomy reservoir, a vertical pole and base supporting said reservoir, at least one intravenous fluid bag mounted on said pole above the reservoir and in fluid communication with the reservoir, fluid conduit means providing a recirculatory loop communicating from and returning to the reservoir, an air embolus detector in a near downstream location relative to the reservoir in the loop and mounted on the pole, a roller pump in the loop downstream of the air embolus detector, the roller pump being mounted on the base, a heat exchanger in the loop and mounted on the pole, a bubble trap-filter in a far downstream location relative to the reservoir in the loop and mounted on the pole said bubble trap filter having an inlet and outlet, said fluid conduit means including tubing means in fluid communication with the filter outlet at one end and with the reservoir at a second end to complete the recirculatory loop, and separate means in fluid communication with the tubing means between the bubble trap-filter outlet and reservoir to selectably discharge fluid from the loop to a patient, said discharge means being downstream of the bubble trap-filter, said mountings on said pole being easily detachable from said pole.

* * * * *